(12) United States Patent
Morii et al.

(10) Patent No.: US 11,179,133 B2
(45) Date of Patent: Nov. 23, 2021

(54) COLLIMATER, RADIATION DETECTION DEVICE, AND RADIATION INSPECTION DEVICE

(71) Applicant: ANSEEN INC., Hamamatsu (JP)

(72) Inventors: Hisashi Morii, Hamamatsu (JP); Takaharu Okunoyama, Hamamatsu (JP); Katsuyuki Takagi, Hamamatsu (JP)

(73) Assignee: ANSEEN INC., Hamamatsu (JP)

( * ) Notice: Subject to any disclaimer, the term of this patent is extended or adjusted under 35 U.S.C. 154(b) by 0 days.

(21) Appl. No.: 16/976,371

(22) PCT Filed: Feb. 27, 2018

(86) PCT No.: PCT/JP2018/007361
§ 371 (c)(1),
(2) Date: Aug. 27, 2020

(87) PCT Pub. No.: WO2019/167145
PCT Pub. Date: Sep. 6, 2019

(65) Prior Publication Data
US 2021/0045705 A1 Feb. 18, 2021

(51) Int. Cl.
*A61B 6/00* (2006.01)
*A61B 6/03* (2006.01)
*A61B 6/10* (2006.01)

(52) U.S. Cl.
CPC .......... *A61B 6/5282* (2013.01); *A61B 6/032* (2013.01); *A61B 6/107* (2013.01); *A61B 6/4291* (2013.01)

(58) Field of Classification Search
CPC ..... A61B 6/5282; A61B 6/4291; A61B 6/107; A61B 6/032; A61B 6/58; A61B 6/06;
(Continued)

(56) References Cited

U.S. PATENT DOCUMENTS 4,446,570 A 5/1984 Guth
5,581,592 A * 12/1996 Zarnoch ................. G21K 1/025
378/149
(Continued)

FOREIGN PATENT DOCUMENTS

CN 104715802 A 6/2015
JP S50-008495 A 1/1975
(Continued)

OTHER PUBLICATIONS

European Office Action and Search Report corresponding to EP Application No. 18908188.8 dated Feb. 2, 2021. (pp. 9).
(Continued)

*Primary Examiner* — Don K Wong
(74) *Attorney, Agent, or Firm* — Muncy, Geissler, Olds and Lowe, P.C.

(57) ABSTRACT

Provided are a collimator, a radiation detection device, and a radiation inspection device that are capable of further removing scattered radiation. This collimator 20 comprises: a radiation blocking section 22; and a radiation transmission section 21 that has a lower radiation blocking rate than the radiation blocking section 22, penetrates the radiation blocking section 22, and is solid. The X-ray transmission section 21 of the collimator 20 is solid therefore X-rays on the low-energy side that have been scattered by a subject B in the X-ray transmission section 21 are absorbed, as a result of this collimator 20. Accordingly, there is little noise contained in X-rays detected by a radiation detection element 30 and a high-resolution X-ray image can be obtained.

7 Claims, 8 Drawing Sheets

(58) Field of Classification Search
CPC ........... A61B 6/03; A61B 6/4216; A61B 6/08; A61B 6/40; A61B 6/42; A61B 6/4035; A61B 6/405; A61B 6/4064; G21K 1/025; G21K 1/00; G21K 7/00; G21K 1/02; G21K 1/08; G01T 1/00
See application file for complete search history.

(56) References Cited

U.S. PATENT DOCUMENTS

| | | | |
|---|---|---|---|
| 6,408,054 | B1 | 6/2002 | Rahn |
| 9,431,141 | B1 | 8/2016 | Burggraf |
| 2008/0088059 | A1* | 4/2008 | Tang .................. G21K 1/025 264/261 |
| 2013/0343524 | A1 | 12/2013 | Teshima |
| 2015/0243397 | A1* | 8/2015 | Yun .................... G21K 1/02 378/36 |
| 2016/0233002 | A1 | 8/2016 | Yokoyama |
| 2018/0000433 | A1 | 1/2018 | Yamamoto et al. |
| 2019/0059846 | A1* | 2/2019 | Jiang .................. A61B 6/032 |

FOREIGN PATENT DOCUMENTS

| | | |
|---|---|---|
| JP | S59-071605 U | 5/1984 |
| JP | S59-159403 U | 10/1984 |
| JP | H04-500276 A | 1/1992 |
| JP | 2001-194462 A | 7/2001 |
| JP | 2001-349992 A | 12/2001 |
| JP | 2009-531126 A | 9/2009 |
| JP | 2012-143396 A | 8/2012 |
| JP | 2012-149982 A | 8/2012 |
| JP | 2014-006194 A | 1/2014 |
| JP | 2014-170008 A | 9/2014 |
| JP | 2015-203571 A | 11/2015 |
| JP | 2018-000496 A | 1/2018 |
| WO | WO-90/15420 A1 | 12/1990 |
| WO | WO-2007/111549 A1 | 10/2007 |

OTHER PUBLICATIONS

An Office Action corresponding to KR Patent Application No. 10-2020-7026007 dated Jan. 6, 2021. (pp. 6).
International Search Report (with English translation) and Written Opinion dated Jun. 26, 2018 issued in corresponding Application No. PCT/JP2018/007361.
Notice of Reasons for Rejection dated Feb. 28, 2019 issued to JP Application No. 2018-566995, dated Mar. 5, 2019.
Notice of Decision of Rejection dated Jun. 6, 2019 issued to JP Application No. 2018-566995, dated Jun. 11, 2019.
Notice of Decision of Grant a Patent dated Oct. 3, 2019 issued to JP Application No. 2018-566995, dated Oct. 8, 2019.
Notice of Reasons for Rejection issued to TW Application No. 108102490, dated Nov. 8, 2019.
Notice of Decision of Grant a Patent issued to TW Application No. 108102490, dated May 12, 2020.

* cited by examiner

COLLIMATER, RADIATION DETECTION DEVICE, AND RADIATION INSPECTION DEVICE

TECHNICAL FIELD

The present invention relates to a collimator, radiation detection device, and radiation inspection device.

BACKGROUND ART

Radiation inspection devices that perform nondestructive testing, such as, for example, X-ray computed tomography (CT) devices, irradiate a subject with radiation and generate a CT image based on the radiation transmitted through the subject.

This kind of radiation inspection device is equipped with a radiation emitting device and a radiation detection device. The radiation irradiated onto the subject is partially scattered inside the subject. When the radiation detection device detects scattered radiation, detection accuracy deteriorates. In order to remove this scattered radiation, the radiation detection device is provided with a collimator.

Collimators are conventionally provided with a plurality of through holes that transmit radiation. When radiation passes through these through holes, radiation that enters a through hole at an angle equal to or greater than a predetermined angle relative to a central axis of the through hole collides with the sidewall of the through hole. Since scattered radiation that degrades detection accuracy is oriented in various directions, it is removed when passing through the through holes, resulting in a more accurate CT image compared to when no collimator is provided (See, for example, Patent Document 1).

Patent Document 1: Japanese Unexamined Patent Application, Publication No. 2018-00496

DISCLOSURE OF THE INVENTION

Problems to be Solved by the Invention

However, as not all of the scattered radiation is removed from the radiation that has passed through the through holes, it still contains a certain amount of scattered radiation.

It is an object of the present invention to provide a collimator, a radiation detection device, and a radiation inspection device that are capable of further removing scattered radiation.

Means for Solving the Problems

In order to solve the above problem, the present invention provides the following.

A collimator including a radiation blocking section, and a radiation transmission section that has a lower radiation blocking rate than the radiation blocking section, penetrates the radiation blocking section, and is solid.

The radiation transmission section may be made of a material that has a high visible light transmittance.

The radiation transmission section may be made of carbon.

The radiation blocking section may be made of tin.

Further, in order to solve the above problem, the present invention provides the following.

A collimator including a liquid radiation blocking section, a radiation transmission section that has a lower radiation blocking rate than the radiation blocking section and penetrates the radiation blocking section, and a container that encloses the radiation blocking section and the radiation transmission section.

In addition, in order to solve the above problem, the present invention provides the following.

A radiation detection device including the collimator according to any of the above descriptions, and a detection element arranged in correspondence with the radiation transmission section.

Further, in order to solve the above problem, the present invention provides the following.

A radiation inspection device including a radiation emitting unit that irradiates a subject with radiation, the collimator according to any of the above descriptions, and a detection element arranged in correspondence with the radiation transmission section.

Effects of the Invention

According to the present invention, eliminating the need for a light-blocking plate makes it possible to provide a collimator, a radiation detection device, and a radiation inspection device, the production process of which can be simplified, and which can be produced in a more compact form.

PREFERRED MODE FOR CARRYING OUT THE INVENTION

Figure 1:
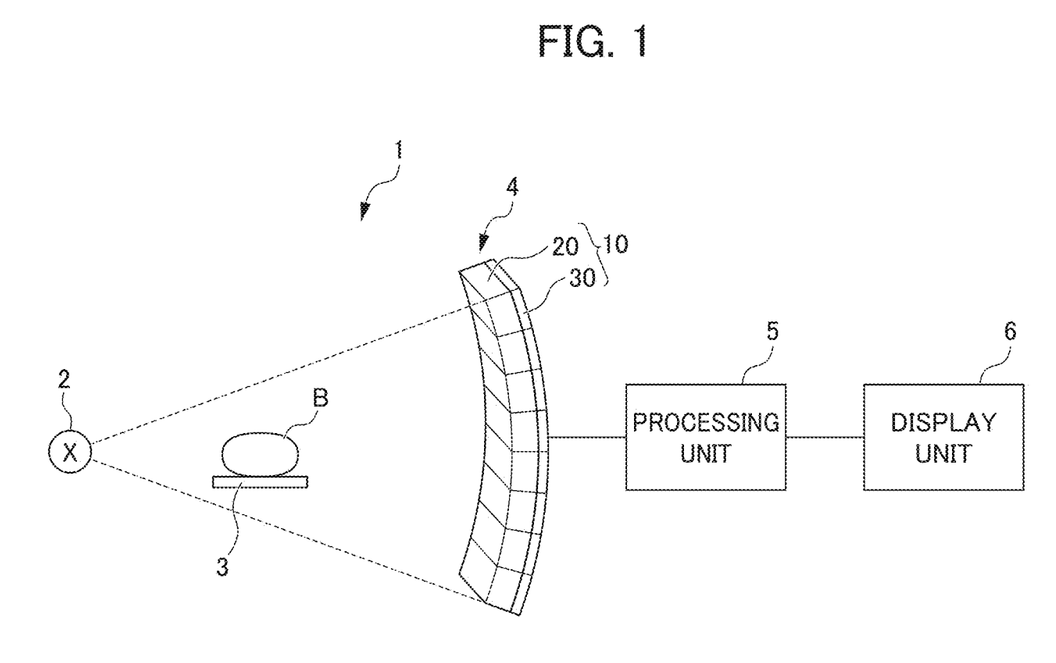
FIG. 1 is a schematic view of an X-ray CT device 1 which is an embodiment of a radiation inspection device.

FIG. 1 is a schematic view of an X-ray CT device (X-ray inspection device) 1 which is an embodiment of a radiation inspection device according to the present invention. It should be noted that the present invention is not limited to the X-ray CT device 1, but may also be a radiation inspection device using other radiation such as gamma rays, etc.

The X-ray CT device 1 includes an X-ray emitting device (radiation emitting device) 2, a platform 3 on which a subject B is placed, and an X-ray detection device (radiation detection device) 4 arranged along a circumference centered on the X-ray emitting device 2. The X-ray detection device 4 includes a plurality of X-ray detection units (radiation detection units) 10.

First Embodiment

Figure 2:
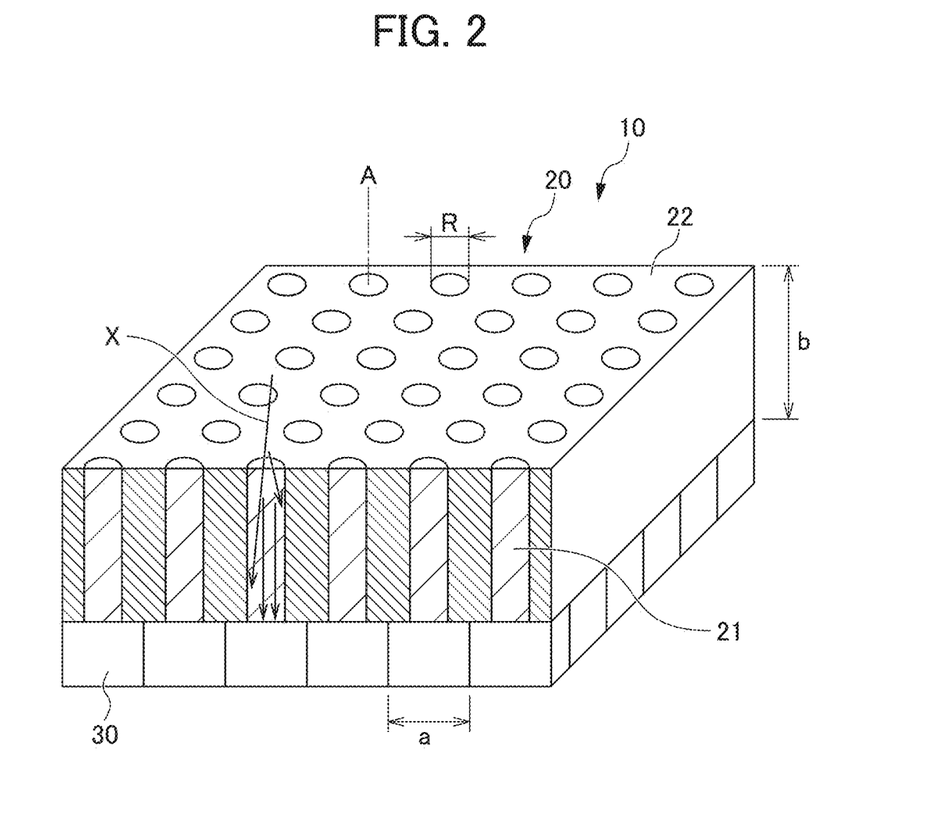
FIG. 2A is a cross-sectional perspective view of one X-ray detection unit 10 according to a first embodiment.
FIG. 2B is a cross-sectional perspective view of one X-ray detection unit 10 according to a first embodiment.
FIG. 2C is a cross-sectional perspective view of one X-ray detection unit 10 according to a first embodiment.
FIG. 2D is a cross-sectional perspective view of one X-ray detection unit 10 according to a first embodiment.
FIG. 2E is a cross-sectional perspective view of one X-ray detection unit 10 according to a first embodiment.

FIG. 2 is a cross-sectional perspective view of one X-ray detection unit 10 according to a first embodiment. Each X-ray detection unit 10 includes a collimator 20 and a plurality of X-ray detection elements (radiation detection elements) 30.

The X-ray detection elements 30 are arranged at intervals (pitch) of about 0.1 to 2.00 mm. The X-ray detection elements are arranged in correspondence with respective X-ray transmission sections 21 provided to the collimator 20 described below.

The X-ray detection elements 30 may be of an indirect conversion type or a direct conversion type. An X-ray detection element 30 of an indirect conversion type is composed of a scintillator and an optical sensor such as a photomultiplier, converting incident X-rays into light by the scintillator and converting the converted light into electrical signals by a photoelectric conversion element.

An X-ray detection element 30 of a direct conversion type is composed of a plurality of cadmium telluride (CdTe) semiconductor devices, and converts incident X-rays directly into electrical signals.

(Collimator 20)

The collimator 20 includes an X-ray blocking section (radiation blocking section) 22 in the form of a plate with a predetermined thickness, and a plurality of columnar X-ray transmission sections (radiation transmission sections) 21 arranged in a grid and penetrating the X-ray blocking section 22.

(X-Ray Blocking Section 22)

The X-ray blocking section 22 is made of a material with a high blocking rate (low transmittance) against X-rays and visible light.

In the embodiment, the material of the X-ray blocking section 22 is tin. However, this is not a limitation, and the material of the X-ray blocking section 22 may be a metal with a high atomic number, high X-ray blocking capability (stopping power) against visible light and X-rays, or which is heavy, such as molybdenum, tantalum, lead, tungsten, etc., or an alloy containing these heavy metals. It should be noted that the melting point of tin is 231° C., and when carrying out the production method described below, the use of a metal with a comparatively low melting point about the same as that of tin facilitates production. A thickness b of the X-ray blocking section 22 is about 1 to 50 mm.

(X-Ray Transmission Section 21)

In the embodiment, the X-ray transmission section 21 is, for example, columnar in shape, solid, and a central axis A of the column extends in a direction respectively toward the X-ray emitting device 2 or the subject B. To the face of the X-ray transmission section 21 on the opposite side from the X-ray emitting device 2 or the subject B is provided with a respective X-ray detection element 30 which is tightly attached so that visible light cannot enter between the X-ray transmission section 21 and the X-ray detection element 30.

A radius R of the X-ray transmission section 21 is about 0.07 to 0.2 mm, and the depth of the X-ray transmission section 21 is about 1 to 50 mm, equal to the thickness b of the X-ray blocking section 22. In other words, the radius R of the X-ray transmission section 21 is of a smaller shape (elongated shape with a high aspect ratio) compared to the depth b. It should be noted that the X-ray transmission section 21 is not limited to a columnar shape, but may also be in the shape of an elliptical column or a polygonal column.

The X-ray transmission section 21 is made of a material with a low blocking rate (high transmittance) against X-rays and a high blocking rate (low transmittance) against visible light, such as carbon.

However, this is not a limitation, and the material may be a material other than carbon, having an atomic number smaller than that of the X-ray blocking section 22, a low X-ray blocking rate, or which is light, such as aluminum.

Further, when carrying out the production method described below, the melting point of the material of the X-ray transmission section 21 is higher than the melting point of the material of the X-ray blocking section 22.

(Operation of the X-Ray CT Device 1)

Next, an operation of the X-ray CT device 1 according to the present embodiment will be described.

X-rays emitted by the X-ray emitting device 2 are irradiated onto the subject B. The light irradiated onto the subject B is transmitted through the subject B, where the light is partially scattered. X-rays proceeding straight after passing through the subject B and scattered X-rays which have been scattered in the subject B reach the collimator 20.

Of the X-rays that have reached the collimator 20, X-rays other than the X-rays that enter the X-ray transmission section 21 are blocked by the X-ray blocking section 22 due to the high X-ray blocking rate of the X-ray blocking section 22.

Meanwhile, the X-rays that have reached the X-ray transmission section 21 enter the X-ray transmission section 21, as the X-ray blocking rate of the X-ray transmission section is low. Visible light is blocked due to the high blocking rate against visible light of the X-ray transmission section 21.

Of the X-rays that have entered the inside of the X-ray transmission section 21, scattered X-rays that are at an angle equal to or greater than a predetermined angle relative to the central axis A of the X-ray transmission section 21 will hit the side surface of the X-ray transmission section 21 before passing through the X-ray transmission section 21, and are thus blocked by the X-ray blocking section 22.

As such, of the X-rays that have entered the X-ray transmission section 21, only X-rays travelling sufficiently straight pass through the X-ray transmission section 21 and reach the X-ray detection element 30.

In the case of an indirect conversion type X-ray detection element 30, the X-rays that have reached the X-ray detection element 30 are converted into light by the scintillator, and the converted light is converted into an electrical signal by the photoelectric conversion element. In the case of a direct type X-ray detection element 30, the X-rays are converted directly into an electrical signal.

Intensity information of the X-rays converted into an electrical signal is processed by a processing unit 5 to generate X-ray CT image data, and an X-ray CT image is displayed by a display unit 6.

(Method for Producing the Collimator 20)

FIG. 3 is a drawing describing a method for producing the collimator 20 according to the first embodiment. FIG. 4 is a flowchart describing the method for producing the collimator 20 according to the first embodiment. The collimator 20 according to the first embodiment is produced by casting.

Figure 3A:
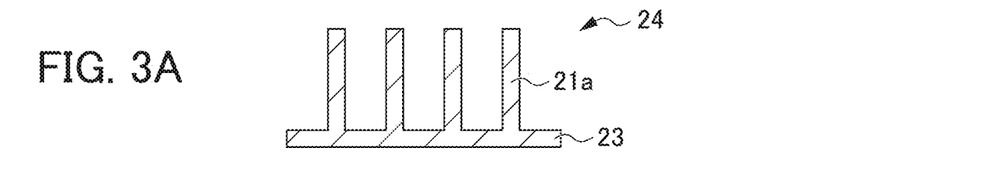
FIG. 3 is a drawing describing a method for producing a collimator 20 according to the first embodiment.
Figure 4:
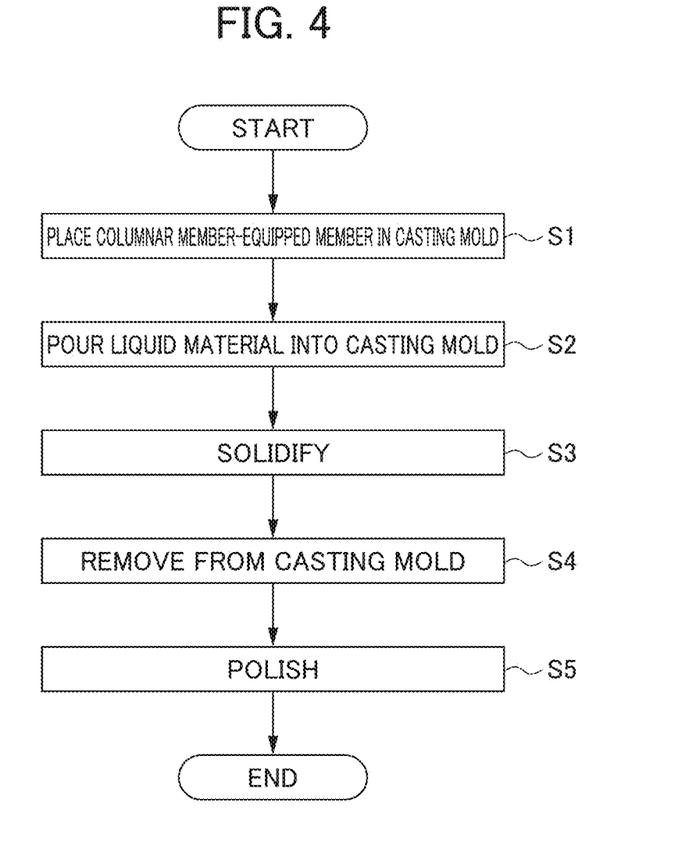
FIG. 4 is a flowchart describing the method for producing the collimator 20 according to the first embodiment.

First, a columnar member-equipped member 24 in which a plurality of columnar members for forming the X-ray transmission section 21 are provided upright on a support substrate 23 is prepared (FIG. 3A).

In the first embodiment, columnar members 21a and the support substrate 23, in other words the columnar member-equipped member 24 as a whole, is made of carbon. However, this is not a limitation, and the columnar members 21a and the support substrate 23 may be separate pieces.

Figure 3B:
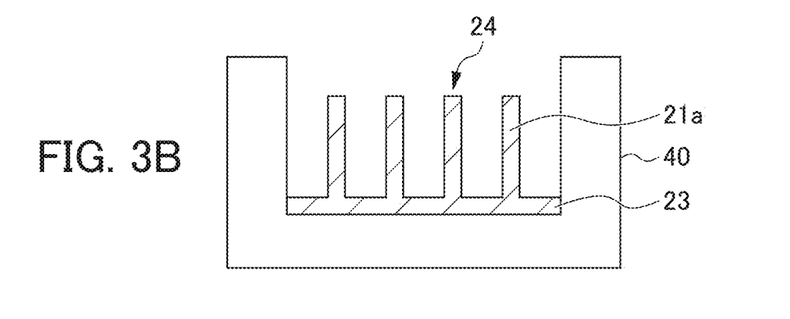

The columnar member-equipped member 24 is placed inside a casting mold 40 (FIG. 3B, FIG. 4 (Step S1)).

Figure 3C:
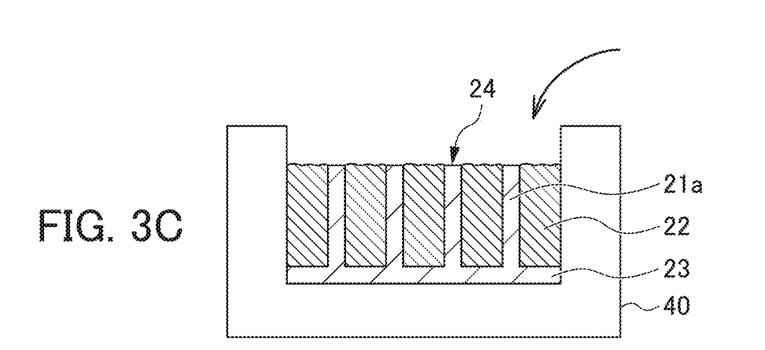

The material of the X-ray blocking section 22, which in the embodiment is tin, which has been heated to its melting point or more to become liquid, is poured into the casting mold 40 (FIG. 3C, FIG. 4 (Step S2)). The melting point of tin is 231° C.

The temperature is lowered to the melting point or less in order to solidify the X-ray blocking section 22 (FIG. 4 (Step S3)).

Figure 3D:
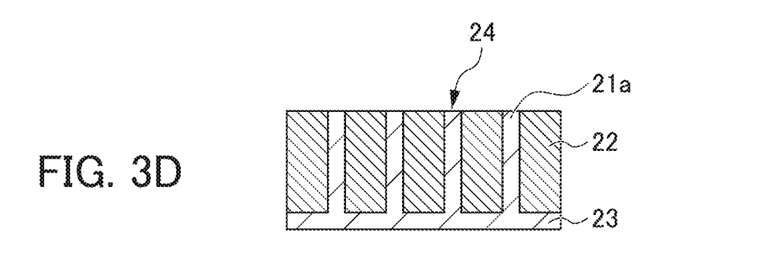

The X-ray blocking section 22, having solidified to become integrated with the columnar member-equipped member 24, is removed from the casting mold 40 (FIG. 3D, FIG. 4 (Step S4)).

Figure 3E:
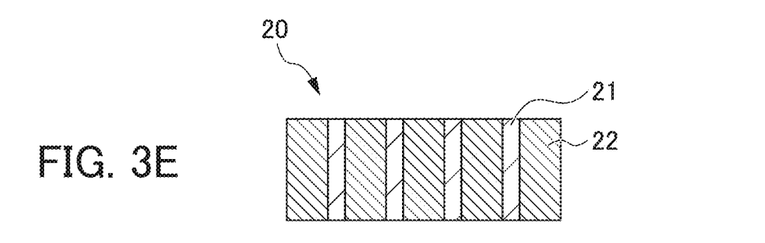

At least the surface of the support substrate 23 of the integrated columnar member-equipped member 24 and X-ray blocking section 22 is polished to remove the support substrate 23 (FIG. 3E, FIG. 4 (Step S5)).

The collimator 20 according to the present embodiment is thus produced.

The effect of the present embodiment is described below.

Figure 5:
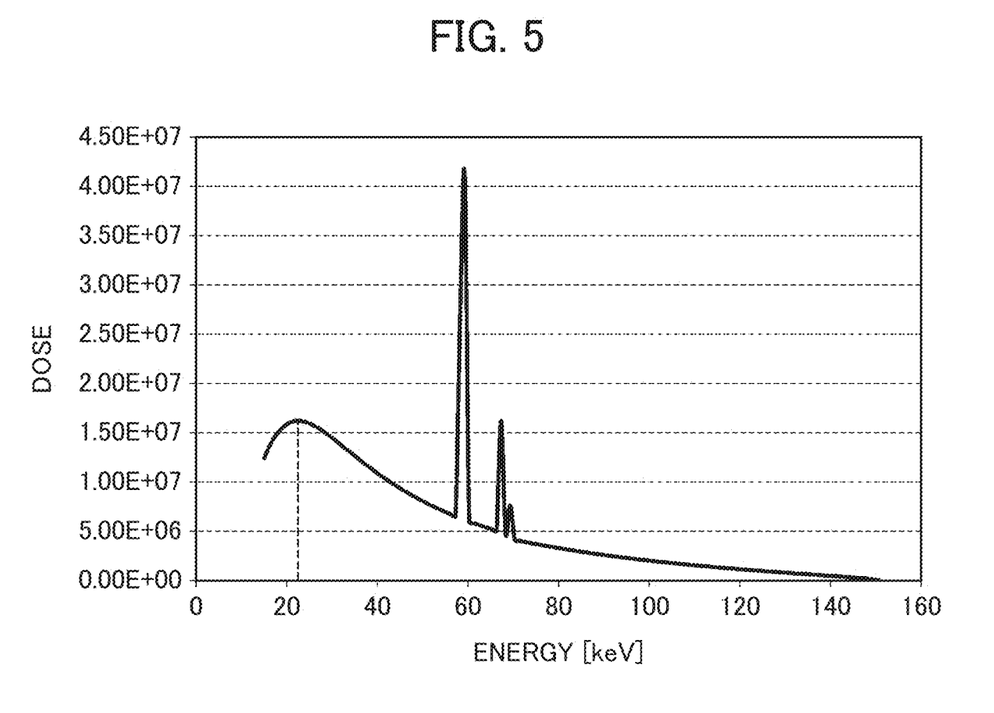
FIG. 5 is a graph showing simulation-calculated values of an X-ray spectrum.

(1) FIG. 5 is a graph showing simulation-calculated values of an X-ray spectrum of one example of an X-ray source that is preferable used as the X-ray emitting device 2, wherein the Y-axis represents X-ray dose and the X-axis represents X-ray energy. As illustrated, in the X-ray spectrum according to this example, the dose peaks at around 22 keV of energy, and the dose decreases as the energy becomes higher. The dose also decreases at a lower energy than around 22 keV.

Figure 6:
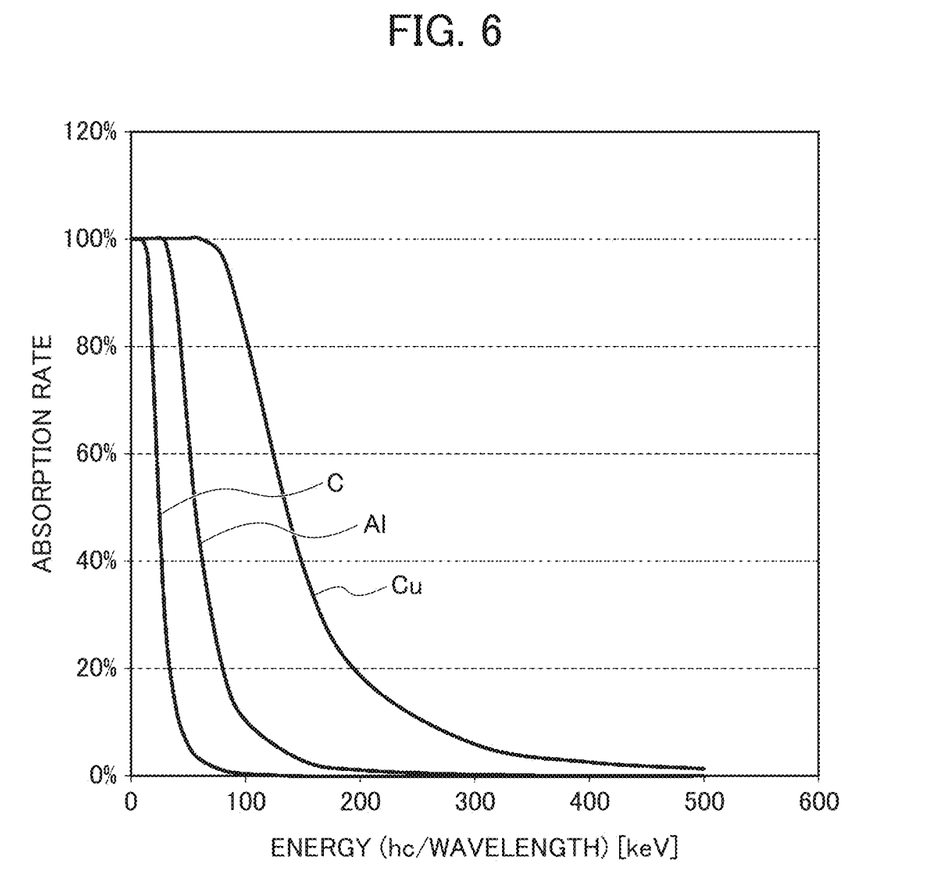
FIG. 6 is a graph showing X-ray absorption rates of carbon (C), aluminum (Al), and copper (Cu)

FIG. 6 is a graph showing the X-ray absorption rates of carbon (C), aluminum (Al), and copper (Cu), each with a thickness of 30 mm. As illustrated, carbon (C), aluminum (Al), and copper (Cu) have low absorption rates of high-energy X-rays, and high absorption rates of low-energy X-rays.

In particular, carbon has a high selective absorption of low-energy X-rays, and while the absorption rate is approximately 0% at an energy of about 150 keV or more, the absorption rate increases drastically when the energy is lower than about 150 keV. This selective absorption becomes higher in the order of copper (Cu), aluminum (Al), and carbon (C).

Figure 7:
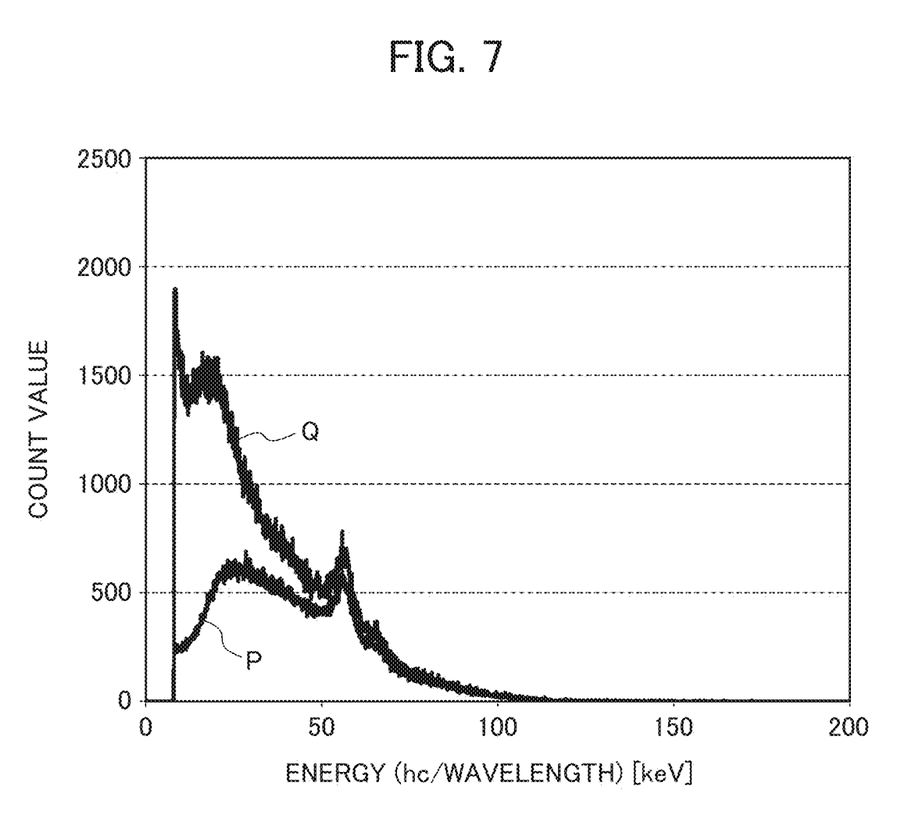
FIG. 7 is a graph showing a count value of X-rays emitted by an X-ray emitting device 2, irradiated onto a subject B, and detected by an X-ray detection element 30.

FIG. 7 is a graph showing a count value of X-rays emitted by an X-ray emitting device 2 using an X-ray source having the spectrum shown in FIG. 5, irradiated onto a subject B, and detected by an X-ray detection element 30. Count value P represents a case in which a collimator 20 of the embodiment that has actually been produced is arranged between the X-ray detection element 30 and the subject B, and count value Q represents a case in which the collimator itself is not arranged between the X-ray detection element 30 and the subject B. As the collimator 20, a collimator was used in which tin with a thickness of 30 mm was used as the X-ray blocking section 22, and the X-ray transmission section 21 was formed by filling through holes with a diameter of 0.2 mm and a length of 30 mm with carbon.

As shown by the count value Q, in the case in which the collimator itself is not arranged between the X-ray detection element 30 and the subject B, the X-rays detected by the X-ray detection element 30 include a large amount of low-energy X-rays which have been scattered in the subject B and thus have reduced energy. Therefore, a high-resolution X-ray image cannot be obtained.

By contrast, in the case in which the collimator 20 filled with carbon of the embodiment that has actually been produced is arranged between the X-ray detection element 30 and the subject B, the low-energy X-rays that have been scattered in the subject B are absorbed (blocked) in the X-ray transmission section 21, as shown in FIG. 6. Therefore, as shown by the count value P, X-rays with an energy distribution (shape of the curve) similar to the shape of the X-ray spectrum represented by the simulation-calculated values (FIG. 5) can be detected.

In other words, according to the collimator 20 of the embodiment, scattered X-rays can better be removed, which decreases noise included in the X-rays detected by the X-ray detection element 30 and allows for a high-resolution X-ray image to be obtained.

It should be noted that the X-ray transmission section 21 is not limited to carbon, but may be made of other appropriately selected materials such as aluminum and copper shown in FIG. 6, allowing for light of an undesired wavelength to be removed depending on the application.

(2) Conventional X-ray detection devices are provided with light-blocking structures to prevent visible light from entering the X-ray detection element. In the case of scintillators in particular, since X-rays are first converted into visible light to be detected, the need to prevent exterior visible light from entering makes the light-blocking structure important.

However, in the present embodiment, the X-ray transmission section 21 of the collimator 20 is filled with carbon and is solid. In addition, the collimator 20 and the X-ray detection element 30 are tightly attached to prevent visible light from entering between them.

Accordingly, since visible light cannot reach the X-ray detection element 30, there is no need to provide a separate light-blocking structure. This can reduce production costs and shorten production time.

(3) For the sake of comparison, it is possible to, for example, provide an X-ray transmission section by opening through holes in an X-ray blocking section by drilling or the like.

However, in order to be able to block X-rays, the X-ray blocking section is made of a metal with a high atomic number. It therefore has a high hardness, which makes it difficult to open fine through holes with low aspect ratios, leading to high production costs and long production time. Further, swarf resulting from drilling the through holes may get caught up in the drill as it continues to rotate, further complicating the opening of precise and fine through holes.

However, the collimator 20 of the present embodiment is made by inserting a support substrate 23 having columnar X-ray transmission sections 21 provided upright thereon into a casting mold 40, into which molten X-ray blocking section 22 material is poured and solidified. As such, unlike a method of opening through holes by drilling, X-ray transmission sections 21 that are fine and have small aspect ratios can easily be produced. This allows for the production of a collimator 20 with a higher directionality.

Second Embodiment

Next, a second embodiment of the present invention will be described. The second embodiment differs from the first embodiment in terms of the structure and production method of a collimator 120. Since the other aspects are the same as in the first embodiment, description of the same portions is omitted. Tin is used for the X-ray blocking section 22 of the collimator 20 of the first embodiment, but for an X-ray blocking section 122 of the collimator 120 of the second embodiment, mercury, which is a liquid at room temperature, is used.

Figure 8A:
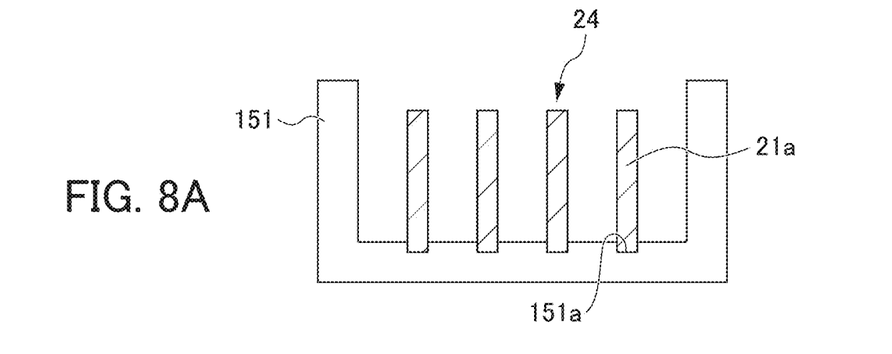
FIG. 8A is a drawing describing a method for producing a collimator 120 according to a second embodiment.
Figure 8B:
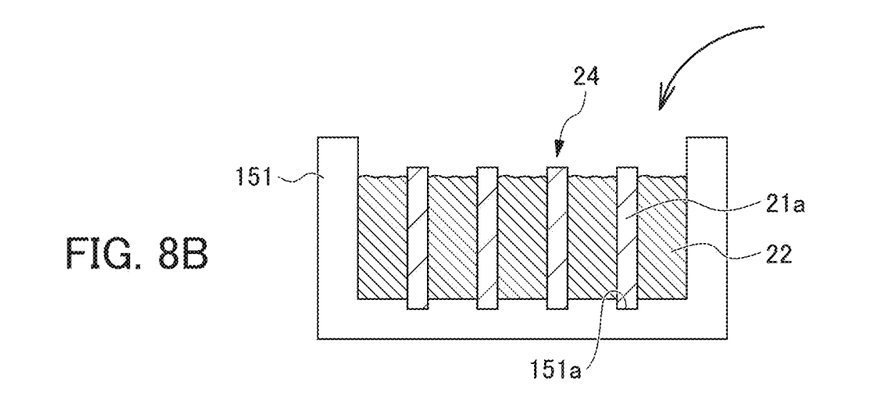
FIG. 8B is a drawing describing a method for producing a collimator 120 according to a second embodiment.
Figure 8C:
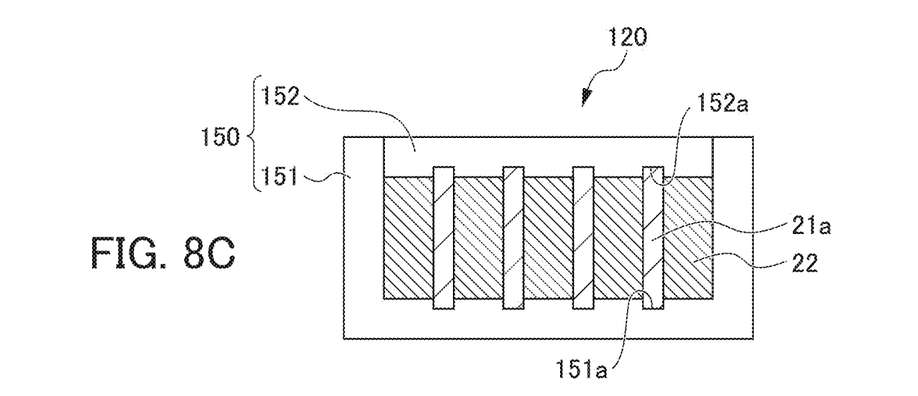
FIG. 8C is a drawing describing a method for producing a collimator 120 according to a second embodiment.

FIG. 8 is a drawing describing a method for producing the collimator 120 according to the second embodiment. As shown in FIG. 8C, the collimator 120 of the second embodiment includes a container 150, a liquid X-ray blocking section 122 of mercury enclosed within the container 150, and a plurality of X-ray transmission sections 121 made of a solid material with a lower X-ray blocking rate than the X-ray blocking section 122 such as carbon and having upper and lower ends fixed to two opposite surfaces in the container 150.

The container 150 includes a lower container 151 with an open top and a lid 152 that covers the top of the lower container 151. The inner surface of the bottom of the lower container 151 is provided with a plurality of blind holes 151a into which the lower ends of the columnar X-ray transmission sections 21 can be inserted to be held in place.

The lower surface of the lid 152 is provided, at positions corresponding to the blind holes 151a, with blind holes 152a into which the upper ends of the columnar X-ray transmission sections 21 can be inserted to be held in place.

The material of the container 150 is preferably a material that is rigid and resistant to corrosion by mercury, such as resin, glass, or ceramic.

The collimator 120 according to the second embodiment is produced as described below.

The X-ray transmission sections 21 are inserted into the blind holes 151a of the lower container 151 to be held in place (FIG. 8A). Mercury, which is to constitute the X-ray blocking section 22, is poured into the lower container 151 (FIG. 8B). At this time, the upper ends of the X-ray transmission sections 121 protrude above the surface of the mercury.

The lid 152 is placed on the lower container 151 to enclose the mercury within the container 150. At this time, the upper ends of the X-ray transmission sections 121 are fitted into the blind holes 152a of the lid 152 (FIG. 8C).

In this way, the collimator 120 of the second embodiment including the liquid X-ray blocking section 122 of mercury enclosed within the container 150, and the plurality of X-ray transmission sections 121 made of a solid material with a lower X-ray blocking rate than the X-ray blocking section 122 such as carbon and having upper and lower ends fixed to two opposite surfaces in the container, is produced.

According to the collimator 120 of the second embodiment, in addition to the effects of the first embodiment, changing the shape of the container 150 allows for production of collimators 120 of various shapes. It is thus possible to easily produce, for example, a curved collimator 120.

In addition, if the material of the container 150 itself is a plastic material, deformation after production is also easy, allowing for the production of a highly versatile collimator 120.

EXPLANATION OF REFERENCE NUMERALS

A Central axis
B Subject
1 X-ray CT device (radiation inspection device)
2 X-ray emitting device (radiation emitting device)
3 Platform
4 X-ray detection device (radiation detection device)
5 Processing unit
6 Display unit
10 X-ray detection unit (radiation detection unit)
20 Collimator
21a Columnar member
21 X-ray transmission section (radiation transmission section)
22 X-ray blocking section (radiation blocking section)
23 Support substrate
24 Columnar member-equipped member
30 X-ray detection element (radiation detection element)
40 Casting mold
120 Collimator
121 X-ray transmission section (radiation transmission section)
122 X-ray blocking section (radiation blocking section)
150 Container
151 Lower container
151a Blind hole
152 Lid
152a Blind hole

The invention claimed is:

1. A collimator comprising:
a radiation blocking section; and
a radiation transmission section that has a lower radiation blocking rate than the radiation blocking section, penetrates the radiation blocking section, and is solid;
wherein the radiation transmission section is columnar in shape, and made of carbon.

2. The collimator according to claim 1, wherein a melting point of the radiation transmission section is higher than a melting point of the radiation blocking section.

3. The collimator according to claim 1, wherein the radiation blocking section is made of tin.

4. A collimator comprising:
a liquid radiation blocking section;
a radiation transmission section that has a lower radiation blocking rate than the radiation blocking section and penetrates the radiation blocking section; and
a container that encloses the radiation blocking section and the radiation transmission section;
wherein the radiation transmission section is columnar in shape, and made of carbon.

5. A radiation detection device comprising:
the collimator according claim 1; and
a detection element arranged in correspondence with the radiation transmission section.

6. A radiation inspection device comprising:
a radiation emitting unit configured to irradiate a subject with radiation;
the collimator according to claim 1 into which radiation that has passed through the subject enters; and
a detection element arranged in correspondence with the radiation transmission section.

7. The collimator according to claim 6, wherein a radius of the radiation transmission section is about 0.07 mm to 0.2 mm and the depth of the radiation transmission section is about 1 mm to 50 mm.

* * * * *